United States Patent
Melker et al.

(10) Patent No.: US 7,785,262 B2
(45) Date of Patent: Aug. 31, 2010

(54) METHOD AND APPARATUS FOR DIAGNOSING RESPIRATORY DISORDERS AND DETERMINING THE DEGREE OF EXACERBATIONS

(75) Inventors: Richard J. Melker, Gainesville, FL (US); Neil R. Euliano, Gainesville, FL (US)

(73) Assignees: University of Florida Research Foundation, Inc., Gainesville, FL (US); Neil Euliano, Gainesville, FL (US)

( * ) Notice: Subject to any disclaimer, the term of this patent is extended or adjusted under 35 U.S.C. 154(b) by 1437 days.

(21) Appl. No.: 11/122,278

(22) Filed: Apr. 25, 2005

(65) Prior Publication Data

US 2006/0241506 A1 Oct. 26, 2006

(51) Int. Cl.
*A61B 5/08* (2006.01)
*A61B 5/02* (2006.01)
(52) U.S. Cl. .................. 600/484; 600/500; 600/529
(58) Field of Classification Search .............. 600/300, 600/301, 481, 483, 484, 500–504, 529–543
See application file for complete search history.

(56) References Cited

U.S. PATENT DOCUMENTS

| 5,490,505 | A  | * | 2/1996  | Diab et al. | 600/323 |
| 6,081,735 | A  | * | 6/2000  | Diab et al. | 600/336 |
| 6,157,850 | A  | * | 12/2000 | Diab et al. | 600/323 |
| RE38,476  | E  | * | 3/2004  | Diab et al. | 600/336 |
| 2002/0128544 | A1 | * | 9/2002 | Diab et al. | 600/323 |
| 2004/0204636 | A1 | * | 10/2004 | Diab et al. | 600/323 |
| 2004/0236196 | A1 | * | 11/2004 | Diab et al. | 600/310 |

\* cited by examiner

*Primary Examiner*—Charles A Marmor, II
*Assistant Examiner*—Navin Natnithithadha
(74) *Attorney, Agent, or Firm*—Timothy H. Van Dyke; Beusse Wolter Sanks Mora & Maire (57) ABSTRACT

Disclosed herein are apparatuses and methods to monitor respiration and abnormal respiration events utilizing plethysmography. The apparatuses and methods provide an alternative to conventional respiration monitoring methods while enabling accurate yet minimally interruptive and invasive monitoring of respiration. The methods and apparatuses may be employed in the context of sleep studies to determine respiratory related sleep disorders.

17 Claims, 7 Drawing Sheets

METHOD AND APPARATUS FOR DIAGNOSING RESPIRATORY DISORDERS AND DETERMINING THE DEGREE OF EXACERBATIONS

BACKGROUND

A wide range of respiratory disorders are characterized by periods of remission interspersed with periods of exacerbation. This group of disorders is known to have a reversible component to the disease processes which can be treated with a wide range of medications and ancillary therapies. These disorders range from obstruction of the upper airway, such as with seasonal allergy which can temporarily result in partial or complete blockage of the nasopharynx to certain types of sleep apnea which result in temporary partial or complete obstruction of the posterior pharynx during phases of the sleep cycle, to disorders of the trachea and bronchi (tracheomalacia, tracheal polyps and warts, and bronchitis) and particularly to disorders of the lower airways, such as asthma, cystic fibrosis and chronic obstructive pulmonary disease (COPD) which are characterized by inflammation and reversible bronchoconstriction. Exacerbations can run the spectrum from mild to life threatening and in many instances it is difficult for the patient, or in the case of a child, for the parent, to gauge the severity of the relapse.

Typically, physical examination by a physician and/or ancillary tests such as spirometry, pulse oximetry and arterial blood gases are used to gauge the degree of exacerbation. For some diseases, which occur periodically or during sleep, it is necessary to admit the patient to the hospital for formal and extensive testing to diagnose the etiology and severity of the disease. Patients with these disorders frequent emergency departments and physician's offices for diagnosis and treatment as it is difficult for them to gauge when a visit is appropriate and thus they consume a considerable amount of healthcare resources, often unnecessarily.

Sleep apnea is the temporary absence or cessation of breathing during sleep, thereby causing oxygen to cease entering the body leading to hypoxemia (lack of oxygen in the blood) and often, for carbon dioxide ($CO_2$) to accumulate in the blood (hypercarbia). In general, when there is lack of oxygen delivery due to sleep apnea, the oxygen saturation ($SpO_2$), i.e., an amount of oxygen in the blood, decreases to an abnormally low level and $CO_2$ can increase to abnormally high levels.

Sleep fragmentation during sleep apnea causes excessive daytime sleepiness (EDS) and hypoxemia during sleep. Chronic declines in oxygen saturation and increased $CO_2$ may cause high blood pressure, arrhythmia, or other serious cardiovascular abnormalities. Occasionally, a decline in oxygen saturation and/or rise in $CO_2$ may even have fatal results by causing a heart attack while a person is sleeping or increasing the likelihood while they are awake. It is reported that about 20 percent of the adult population of the United States suffers from snoring, and about 50 percent of those people that snore suffer from sleep apnea.

Children with sleep apnea display unique symptoms such as decreased attention span, erratic behavior, EDS, irregular sleep, rib cage retraction, and flaring of the ribs. Such children may do poorly in an academic setting and, in the most serious cases, may suffer from mental or psychological disorders. For infants or babies, sleep apnea may cause sudden death during sleep.

Sleep apnea is typically classified into three main types: obstructive, central, and mixed. Obstructive sleep apnea is the most common form of sleep apnea and is characterized by a repeated closing of the upper airway on inspiration. Central sleep apnea occurs when the brain fails to send adequate signals to the diaphragm and lungs during sleep, thereby resulting in decreased respiration. Mixed sleep apnea is a combination of obstructive sleep apnea and central sleep apnea. Regardless of the type of sleep apnea, it results in a decrease in $SpO_2$ and often retention of $CO_2$. Interestingly, children may manifest only $CO_2$ retention, without the classical finding of decreased $SpO_2$. Thus, one of the major tools for diagnosing sleep apnea, pulse oximetry for measuring $SpO_2$, may be of little value in diagnosing sleep apnea in children.

A breathing disorder is clinically classified as sleep apnea when a cessation of breathing lasting for ten or more seconds occurs at least five times an hour or at least thirty times in a seven-hour period. Snoring is a sound made when a soft palate of the upper airway vibrates, and thus, is often a direct indicator of sleep apnea.

Polysomnography (PSG) is a test during which sleep architecture and function and behavioral events during sleep are objectively measured and recorded. See U.S. Patent Publication No. 2002/0165462. More specifically, a number of physiological variables, such as brain waves, eye movement, chin electromyogram, leg electromyogram, electrocardiogram, snoring, blood pressure, respiration, and arterial oxygen saturation, are measured extensively. At the same time, behavioral abnormalities during sleep are recorded with video tape recorders. Trained technicians and sleep specialists read the record to obtain comprehensive results about the severity of snoring, whether arrhythmia occurs, whether blood pressure increases, whether other problems are caused during sleep, and at what points the record differs from normal sleep patterns.

Full polysomnography is, however, quite labor intensive, requires considerable instrumentation and is therefore expensive to conduct. As a result, many sleep laboratories have found it difficult to keep up with the demand for this test, and long waiting lists have become the norm. Further, many patients find it difficult to sleep adequately when monitored and in strange surroundings. Given that obstructive sleep apnea (OSA) is quite prevalent, leads to serious complications and that treatment options exist, it is important that individuals suffering from the disease are identified.

A conventional full overnight PSG includes recording of the following signals: electroencephalogram (EEG), submental electromyogram (EMG), electrooculogram (EOG), respiratory airflow (oronasal flow monitors), respiratory effort (respiratory plethysmography), oxygen saturation (oximetry), electrocardiography (ECG), snoring sounds, and body position. These signals are considered the "gold standard" for the diagnosis of sleep disorders in that they offer a relatively complete collection of parameters from which respiratory events may be identified and SA may be reliably diagnosed. The RR interval, is derived from the ECG and provides the heart rate and arrhythmia recognition. Body position is normally classified as: right side, left side, supine, prone, or up (or sitting erect). Typically, the microphone and the body position sensor are taped over the pharynx. Each signal provides some information to assist in the visual observation and recognition of respiratory events.

Collapse of the upper airway is conventionally defined in PSG studies as when the amplitude of the respiratory airflow decreases by at least 50%, snoring sounds either crescendo or cease, and oxygen desaturation occurs. An obstruction event is confirmed (i.e., desaturation not an artifact) by the recognition of an arousal (i.e., the person awakens to breathe), typically identified by an increase in the frequency of the EEG, an increase in heart rate, or change in snoring pattern. The remaining signals assist in determining specific types of obstruction events. For example, the EEG and EOG signals are used to determine if an obstruction event occurred in non-rapid eye movement (NREM) or rapid eye movement (REM) sleep. The position sensor is used to determine if an airway collapse occurs only or mostly in just one position (typically supine).

A reduction or absence of airflow at the airway opening defines sleep-disordered breathing. Absent airflow for 10 seconds in an adult is defined as apnea, and airflow reduced below a certain amount is hypopnea. Ideally one would measure actual flow with a pneumotachometer of some sort, but in clinical practice this is impractical, and devices that are comfortable and easy to use are substituted. The most widely used are thermistors placed in front of the nose and mouth that detect heating (due to expired gas) and cooling (due to inspired air) of a thermally sensitive resistor. They provide recordings of changes in airflow, but as typically employed are not quantitative instruments. Currently available thermistors are sensitive, but frequently overestimate flow. Also, if they touch the skin, they cease being flow sensors. Measurement of expired $CO_2$ partial pressure is used in some laboratories to detect expiration, but it is not a quantitative measure of flow.

In sum, the inventors have realized that conventional apparatuses and methods for diagnosing sleep apnea and other respiratory disorders have several disadvantages including being difficult to implement, being unable to detect all three types of sleep apnea, being unable to provide accurate and reliable results, and causing discomfort in a subject being monitored.

SUMMARY

Therefore, the inventors have discovered that there is a substantial need in the art for a device and method that will allow patients and their healthcare providers to rapidly and accurately diagnose air obstruction brought about by respiratory disorders and quantify exacerbations so appropriate treatment, if necessary, can be started expeditiously. Further, the inventors have realized that there is a particular need for a small portable device that can be used by the patient in the home or workplace to determine when an exacerbation has occur and whether they are in need of immediate medical attention.

Sleep apnea represents one such disorder in which the instant device and method could be used. In one embodiment it would allow for screening of subjects in the home as the number of hospital beds allocated for sleep studies is far exceeded by the number of patients that require studies. Subjects that are shown to have characteristics of sleep apnea on home screening could then be scheduled for formal studies, but more importantly, subjects who do not have characteristic findings could be excluded, thus reducing the number of negative studies performed in hospitals. Further, the device and method could be used during hospital studies to diagnose patients, such as children, who have types of sleep apnea that are difficult to diagnose with conventional equipment and who often do not tolerate many of the monitoring devices. Sleep apnea will be used as an example of how the instant device and method can be applied, but it is applicable to a wide range of respiratory diseases.

According to one aspect, the subject invention pertains to a method of diagnosing air obstruction events in a patient, said method comprising securing a pulse oximeter probe to a central source site of said patient wherein said probe is configured to generate a signal stream indicative of blood flow at said central source site; processing said signal stream received from said probe to obtain a separate pulsatile arterial component signal and venous impedance component signal; and evaluating said pulsatile arterial component signal, or venous impedance component signal, or both, to determine the occurrence and degree of an air obstruction event. The method allows for the comfortable and non-invasive monitoring of respiratory rate and degree of airway obstruction in the context of sleep studies for diagnosing respiratory related sleep disorders, as well as for a large number of other respiratory conditions characterized by diminished airflow and increased inspiratory and/or expiratory respiratory effort to breath.

According to another aspect, the subject invention pertains to a method of monitoring respiration and/or degree of airway obstruction of a patient. The method supplants the need for uncomfortable and potentially unreliable gas flow sensors placed in or proximal a patient's mouth or nose.

Another aspect of the subject invention pertains to a method of monitoring respiration in a patient, the method comprising securing a pulse oximeter probe to a central source site of the patient wherein the probe is configured to generate a plethysmography signal stream from the central source site; processing the signal stream received from the probe to obtain a separate arterial component signal and venous impedance component signal; and evaluating the arterial component signal, or venous impedance component signal, or both, to determine respiratory rate, occurrence of an inspiratory event, expiratory event, air restriction or air obstruction, or a combination thereof.

Another aspect of the subject invention pertains to a system for monitoring respiration and/or airway obstruction of a patient. The system comprises one or more pulse oximeter probes configured for securement to a central source site of a patient and to generate signals indicative of blood flow at said central source site. The system also comprises a computer communicatingly connected to one or more pulse oximeter probes. The computer comprises a processing module, a first computer-readable program code module for causing the computer to process signals of the one or more pulse oximeter probes to obtain a venous impedance component signal isolated from a pulsatile arterial component signal, and a second computer-readable program code module for causing the computer to analyze the venous impedance component signal to determine an inspiratory event, expiratory event or an air obstruction event, or a combination thereof.

In yet a further aspect, the subject invention pertains to a method of diagnosing a respiratory condition comprising collecting a first dataset of plethysmography signal information from a patient generated during respiration at one or more predetermined resistances; collecting a second dataset of plethysmography signal information from the patient during a period where said patient is suspected of experiencing air restriction or air obstruction; comparing the second dataset to said first dataset; and diagnosing a respiratory condition based on the comparison.

Another aspect of the subject invention is a method to determine the magnitude of change in the pulsatile arterial and venous impedance components of the photoplethysmogram on a patient while their respiratory status is normal or near normal by having the patient breath through a series of graded resistors and to store and use this information to determine the degree and seriousness of airway obstruction during an exacerbation.

These and other advantageous aspects of the invention will be described in further detail herein.

BRIEF DESCRIPTION OF THE DRAWINGS

FIG. 1a shows the effect of airway maneuvers on an AC component (or arterial component) of a photoplethysmography signal; and FIG. 1b shows the effect of maneuvers on the DC component (or venous impedance component).

FIG. 2a shows the arterial component and FIG. 2b shows the venous impedance component.

DETAILED DESCRIPTION

According to one embodiment, the subject invention is directed to a method of diagnosing whether a patient is likely to experience airway obstruction during sleep through the use of photoplethysmography. To the inventors' knowledge, no one has previously thought of using photoplethysmography for such purpose or for the diagnosis of airway obstruction as manifest by an exacerbation of other respiratory diseases. Traditionally, a plethysmography signal stream is typically obtained from a peripheral site such as the finger, or other extremity, which is usually damped and difficult to process and therefore to interpret. The inventors have discovered that obtaining the photoplethysmograph from a central site eliminates much of the background noise and poor signal to noise ratio found in the plethysmograph from a peripheral site, and it is the obtention of this "less noisy" signal that eventually led to the realization that information such as respiration rate, pulsatile arterial blood flow, degree of airway obstruction and venous impedance can be extrapolated.

Typically, photoplethysmography is conducted using one pulse oximeter probe. The raw signal stream obtained from a pulseoximeter probe is related to the amount of light from the LED that hits the photodetector of the pulseoximeter probe. The magnitude of the signal from the photodetector is inversely proportional to the amount of absorption of the light between the LED and the photodetector (greater absorption results in less light exciting the photodetector). The absorbed light is due to multiple factors, including absorption due to tissue, absorption due to venous blood, absorption due to arterial blood, and absorption due to the pulsation of arterial blood with each heart beat. Typically, the raw signal from the photodetector is processed (e.g. removal of artifacts and auto-gain of the signal) in order to obtain an arterial oxygen saturation value and the plethysmograph is largely ignored. Significant confusion and overlap exists in the terminology used in describing various aspects of pulse oximetry. On one hand, the terms AC component and DC component are used to describe the anatomical structures responsible for the plethysmogram (AC component—pulsatile blood flow in arteries, arterioles and possibly capillaries) and the components responsible for attenuating the signal (DC component—venous blood, tissue, bone, etc.) The terms are also used to describe the phasic rapid pulsatile flow in the arteries and arterioles as seen in the plethysmography (AC component) as contrasted with slower (DC) components of the plethysmograph.

As the AC component and DC component can have different meanings in the art, the AC component will also be referred to herein as the "pulsatile arterial" component, and the DC component will also be referred to herein as the "venous impedance" component. Thus, we use the term AC component to describe a component of a processed plethysmographic signal that represents the pulsatile blood flow that is present in the vascular bed being monitored. The DC component, as used herein, is a phasic slower frequency signal that represents the venous impedance of blood in the vascular bed being monitored and is influenced by variations in intrathoracic pressure and venous blood volume. The pulsatile arterial signal has been typically called the plethysmograph and the venous impedance component overlooked, although it is present in the signal and can be isolated as described later. A further distinction must be made between the term "DC component" and the term "DC offset". The popular usage of the term DC component has been described above. The term "DC offset" refers to the amount that the plethysmographic signal is shifted from a baseline that would be present if no light excited the photodiode. The plethysmographic signal is small relative to the magnitude of the DC offset, and "rides" on the DC offset signal. The DC offset varies with the intensity of the LEDS and the amount of light absorbed by the tissues. Thus, if the light path through tissue remains constant, the DC offset increases with increasing LED power, and decreased with less LED power. Alternatively, the DC offset increases as the path of light through the tissues decreases and decreases as the path of light through the tissues increases. Manufacturers usually have circuits built into the pulse oximeter to keep the LED power in a range in which the DC offset will be an adequate signal to discern the photoplethysmograph, but less than that which will oversaturate the photodiode.

According to one signal processing method embodiment of the subject invention, the effects of the individual heart beats in the plethysmograph are separated out from the other information, which is fundamentally a different goal than conventional processing, which is basically to obtain an adequate arterial component and discarding the venous impedance component. Standard practice is to implement a DC removal technique that involves removing the venous impedance component by a low pass filter. This technique, however, does not sufficiently separate all of the data from the two sources of information. The subject processing method obtains a higher fidelity signal, which is critical when dealing with precise measurements of variables for determining, for example, respiratory events in a patient.

In a specific embodiment, the high fidelity pulsatile arterial component and the venous impedance component of the plethysmography signal (previously ignored by those in the art) are achieved by unique signal processing, comprising:

1) discretely selecting the peaks and troughs of the signal (improved noise/artifact rejection can be achieved by looking for peaks and troughs that exist at the expected heart rate, estimated by Fourier or autocorrelation analysis, or from past good data)

2) finding the midpoints (or minimum values) between peaks and troughs 3) extracting the venous impedance component as the interpolated (and possibly smoothed or splined) line that connects these midpoints (or minimum values)

4) extracting the pulsatile arterial component as the raw signal subtracted from the venous impedance component.

This processing is preferably implemented from signals obtained from a central source site, but it could be applied to signals obtained from other sites so long as the fidelity of the signal is sufficiently high and reliable. This technique achieves a nonlinear filter with zero delay and optimally separates the two signals of interest. In view of the teachings herein, those skilled in the art will appreciate that similar techniques for achieving these objectives could also be adapted, and are differentiated from the conventional processing of plethysmography signals due to their goal of optimally separating the two signals of interest on a beat-to-beat, zero delay basis (unlike standard linear filtering, DC removal techniques, and averaging techniques).

The AC and DC components, as described herein, are intended to be the time varying signals that are related to the beat-to-beat variations caused by the pulsation and therefore, when recorded over time, the flow of blood in the arteries (the AC component, although different from the AC component described by others), and the slowly varying components that are related to the other physiologic and physical properties of the signal related to the impedance of the venous vessels and the changes in intrathoracic pressure, the venous (DC) component which differs from the "classical" description of the DC component which is said to include non-pulsatile arterial blood, pulsatile and non-pulsatile venous blood and tissue and bone. The amplitude and area under the curve (AUC) of the AC component contains information about the amount of arterial blood flowing past the detector. In order to correctly interpret this information, the AC and DC components must be separated more rigorously than with the algorithms in standard monitors and previously described in the literature. In particular, the pulsatile arterial component should contain only that information that relates to beat-to-beat variations of the heart. The DC component should contain lower frequency effects from physiology (such as the respiratory effects, blood pooling, venous impedance, etc.) and physical sensor changes (e.g. changes in the orientation of the probe, etc.).

Accordingly, the inventors have discovered and characterized for the first time at least three separate components of the plethysmograph signal: (a) blood pulsation signal, (b) time-varying DC signal or venous impedance signal, and (c) the classical DC component signal which is a function of the tissue (muscle, bone, etc) at the probe site, and is the baseline DC component on which the venous impedance signal rides.

Pulse oximeter probes useful in accordance with the teachings herein include, but are not limited to, those described in co-pending U.S. application Ser. Nos. 10/176,310; 10/751, 308; 10/749,471; and 60/600,548, the disclosures of which are all incorporated herein in their entirety.

As referred to above, the DC offset (component) of the plethysmogram is an indicator of venous impedance, while the arterial component is a measure of regional blood flow. During forced airway maneuvers, intrathoracic pressure changes dramatically. These pressure changes are transmitted directly to the veins in the head, because there are no anatomical valves in veins leading to the head. Changes in intrathoracic pressure have direct effects on both the beat to beat pulsatile arterial blood flow (AC component) and the amount of venous blood in the vascular bed being monitored on a breath to breath basis. These effects are present even during quiet breathing, but are far more pronounced with "airway maneuvers" such as the Valsalva and Mueller maneuvers, and during exacerbation of respiratory conditions which increase airway resistance and/or decrease lung compliance. These pronounced changes are often referred to as "pulsus paradoxus" when measured by arterial blood pressure or direct arterial blood monitoring. All conditions which affect airway resistance (increase) and lung compliance (decreased) increase the respiratory muscle work (work of breathing for each breath, or power of breathing for the amount of work performed in one minute). As the work or power of breathing increases, there are wider swings in intrathoracic pressure which in turn lead to phasic variations in pulsatile arterial blood flow and venous impedance. Respiratory rate can be easily determined when monitoring at "central source sites" and the degree of change in both the AC and DC components are proportional to the degree of airway obstruction and/or lung compliance. At a given level of resistance and or compliance, variations in the amplitude and AUC of both components can also be an indication of volume status. Thus, a plethora of information on both respiratory and cardiopulmonary mechanics can be ascertained from the processed plethysmograph, especially when it is obtained from a "central source site".

The term "central source site" as used herein refers to a site at or above the patient's neck. Particularly preferred central source sites, include, but are not limited to, a patient's nasal septum, nasal alar, pre-auricular region, post auricular region, tongue, forehead, or cheek, ear canal, or combinations thereof.

The term "obstruction" as used in the context of respiration refers to a blockage of air flow. The blockage may be partial or complete. The term "restriction" as used in the context of respiration is related to obstruction, and in some instances interchangeable with obstruction, and refers to a restriction of air flow. For example, partial obstruction of air flow is interchangeable with restriction and complete restriction is interchangeable with complete obstruction. Unless otherwise indicated herein, restriction refers to a partial obstruction, i.e., some air is allowed to pass, and obstruction refers to complete blockage of air flow.

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information. A computer, as used herein, is a device that comprises at least one processing module.

As will be appreciated by one of skill in the art, embodiments of the present invention may be embodied as a device, method, or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of certain embodiments of the present invention may be written in an object oriented and/or conventional procedural programming languages including, but not limited to, Java, Smalltalk, Perl, Python, Ruby, Lisp, PHP, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain embodiments of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

During airway maneuvers or with many pulmonary diseases intrathoracic pressure increases above ambient pressure during exhalation (e.g., asthma, COPD, Valsalva, exhalation through a resistor). Likewise, airway maneuvers or pulmonary diseases can cause greater than normal decreases in intrathoracic pressuring during inspiration (e.g., Mueller maneuver, asthma, COPD, obstructive sleep apnea, inspiration through a resistor). Using the example of an asthmatic patient, between asthmatic episodes breathing spontaneously, airway resistance is normal or near normal, therefore there should be little phasic change in the arterial component, and only small changes in the venous impedance component. Additionally, if the patient breathes at a prescribed flow rate through graded resistors of known sizes, there should be phasic changes in the arterial and venous impedance components of the plethysmogram. By adding resistance, great excursions in the arterial and venous impedance components are affected. The arterial component develops an increasingly apparent "saw tooth" pattern and the venous impedance component will have wider swings above and below baseline. By calibrating these changes using resistors while a patient is well, these degrees of change can be correlated with each resistor. As such, a patient respiratory profile is created. When the patient is symptomatic, the arterial and venous impedance component changes should reflect the degree of bronchiolar obstruction/resistance equivalent to that seen when breathing through resistors. This can be particularly valuable in determining the degree and seriousness of obstruction and the response to therapy. If either a high degree of obstruction is diagnosed, or there is a poor response to therapy, the patient should present to the Emergency Department (ED). The same measurements can be used in the ED or hospital to follow the course of treatment. Once a profile of arterial and venous impedance response to resistors is obtained for a patient, the profile can be stored in a database and used whenever the patient has an exacerbation. Similar profiles can be obtained on patients with a wide range of respiratory diseases, and can be obtained between exacerbations, or if the patient is having an exacerbation, the changes in the arterial and venous impedance changes can be correlated with measurements made with conventional respiratory monitors, such as a spirometer.

In certain method embodiments, the present invention can monitor and detect respiratory problems caused by disorders, including but not limited to, obstruction of the upper airway, such as with seasonal allergy which can temporarily result in partial or complete blockage of the nasopharynx to certain types of sleep apnea which result in temporary partial or complete obstruction of the posterior pharynx during phases of the sleep cycle, to disorders of the trachea and bronchi (tracheomalacia, tracheal polyps and warts, and bronchitis) and particularly to disorders of the lower airways, such as asthma, cystic fibrosis and chronic obstructive pulmonary disease (COPD) which are characterized by inflammation and reversible bronchoconstriction.

During an obstructive event, it is the inventors' belief that each exhalation will cause increased thoracic pressure and each inhalation will cause decreased thoracic pressure compared to breathing without obstruction. The inventors have realized that this increased thoracic pressure will cause an attenuation of the AC component (less blood flow per beat) and a decrease in the "DC component" (less venous return). The decreased thoracic pressure during inhalation will cause an increase in the DC component (more venous return) and have a smaller effect on the AC component. By measuring these changes during a known calibration period with known resistors, a comparison of the AC and DC changes can be made with the known resistor changes. Each breath will provide dramatic swings in the AC and DC components. Therefore, one method embodiment for determining airway occlusion severity includes the following: record data from normal quiet breathing and conscious slow breathing from a series of breaths (e.g, 5, 10, 15, 20 etc. breaths), followed by recording plethysmographic data from similar breathing with resistors as described in Example 2 above. The data obtained may be put in a table form. The data collected may be modulated with appropriate outlier and noise rejection. Optionally, this data may be compared to the calibration data tables collected on a population of patients to ensure its validity and possibly classify or cluster the patient with responses from other known patients. From the calibration table, a level of occlusion (or an estimated airway resistance) can be determined dynamically by comparing the changes in AC/DC components with the recorded data during calibration. Those skilled in the art will appreciate that these values could also be used in a classification scenario where the patient is deemed to have degrees of occlusion based upon different ranges of resistance (e.g. resistance>40 (units are $cmH_2O/L/sec$ if you are referring to resistance)=total occlusion, resistance<40 but >20=partial occlusion, etc.).

In a specific embodiment, a hand-held or otherwise transportable monitoring device is provided and a patient calibrates the device using a series of resistors. The device may have different function modes, such as a calibration mode and a monitoring mode to assist in this process. During the calibration mode, the device is calibrated to obtain AC/DC component values pertaining to inspiratory and/or expiratory resistors at increasing levels of resistance. These values are stored in the device. When it is suspected that the patient is experiencing a level of obstruction, the patient is monitored with the device in a monitoring mode. During monitoring mode, the AC and/or DC component values are observed and compared to those obtained during calibration mode. The device preferably has a readout screen to display information, and is preferably configured to display the degree of severity of the obstruction event. This device and methodology may be implemented to monitor the presence and/or severity of air obstruction events for different respiratory conditions. In addition, this methodology will provide information regarding the type of air obstruction event, i.e., inspiratory and/or expiratory which will greatly assist in diagnosis of a person's respiratory problem.

EXAMPLE 1

Figure 1:
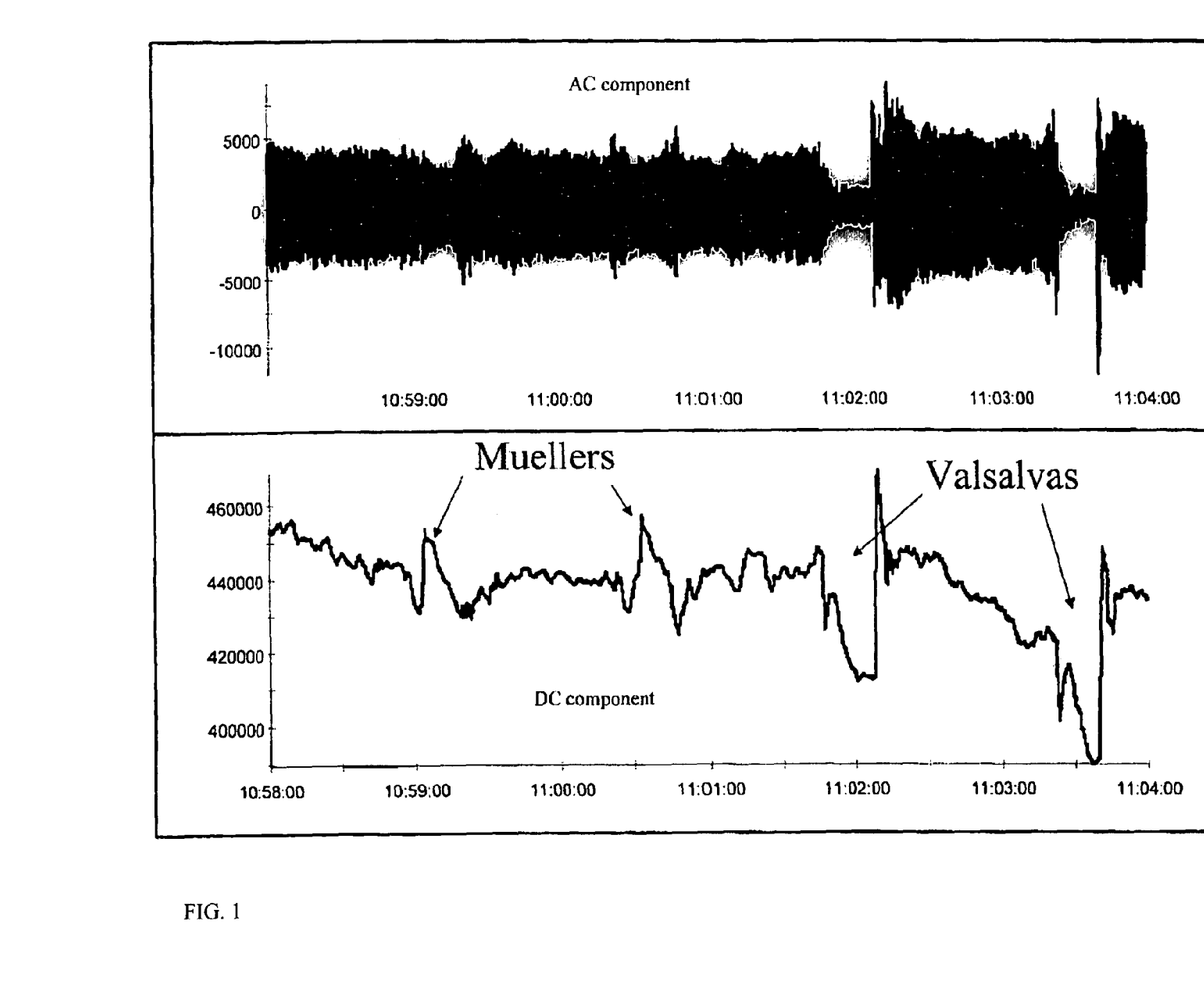
FIG. 1. represents graphs demonstrating the effects of airway maneuvers on photoplethysmography when obtained from a central site.
Figure 2:
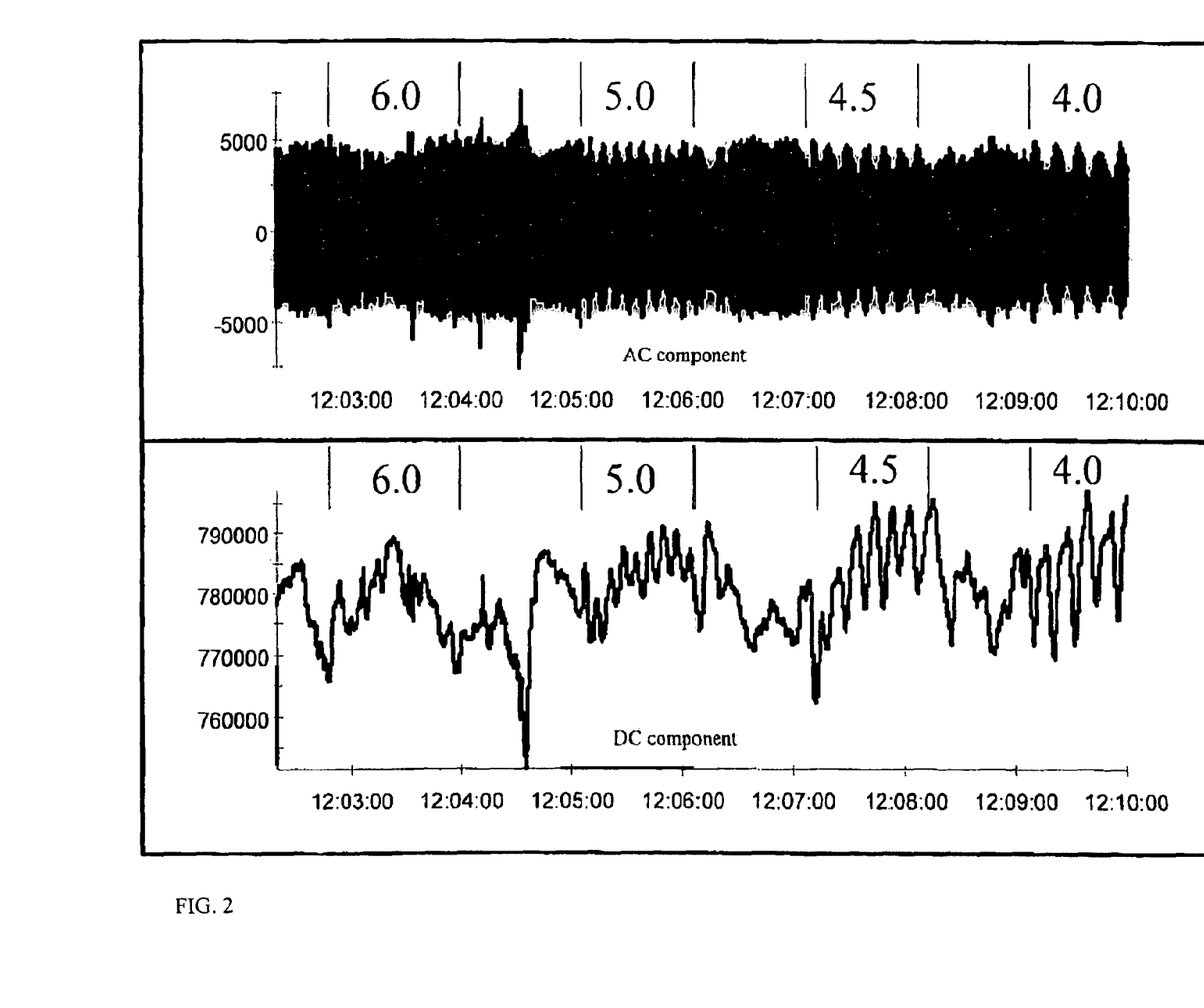
FIG. 2. represents graphs showing the effects of breathing through a series resistors on the photoplethysmography signal obtained from a central site.

FIGS. 1 and 2 demonstrate the ability of photoplethysmography to detect and differentiate different types of airway obstruction. FIG. 1 demonstrates the effects of performing Mueller and Valsalva maneuvers on the photoplethysmogram. Mueller maneuvers, which simulate obstructive sleep apnea (i.e., inspiratory obstruction/resistance, reproducibly show an increase in the venous impedance component due to the increase venous return induced by increased negative intrathoracic pressure. Valsalva maneuvers simulate expiratory obstruction as seen in asthma and to a lesser extent in obstructive sleep apnea. Valsalva maneuvers result in a drop in the venous impedance component due to trapping of venous blood in the head secondary to increased positive intrathoracic pressure.

EXAMPLE 2

FIG. 2 demonstrates the effects of breathing through tubes of increasingly narrower diameter. The subject breathed through each tube for 1 minute and then normally for one minute. The data clearly shows that as the diameter of the tube gets smaller, there are increased swings in both the arterial component and venous impedance component due to increasingly wider swings in intrathoracic pressure. The arterial component takes on its characteristic saw-tooth pattern during respiration through the resistors.

Accordingly, in the context of a sleep study, a patient believed to suffer from obstructive sleep apnea breathes through a series of resistors during inspiration prior to going to sleep. The changes in the AC and venous impedance components can be recorded for several resistors. This information can be stored in a proper storage medium. While the patient is sleeping, the degree of inspiratory airway obstruction can be more accurately gauged by calibrating the signal, i.e., comparing the changes in the arterial and venous impedance components with those obtained during the patient breathing through resistors before going to sleep. The resistors may configure such that they only resist either inspiratory air flow or expiratory air flow. This will further augment the patient's profile to facilitate differentiation of the type of obstruction or restriction a patient is suffering from and therefore more accurate diagnosis.

EXAMPLE 3

Figure 3:
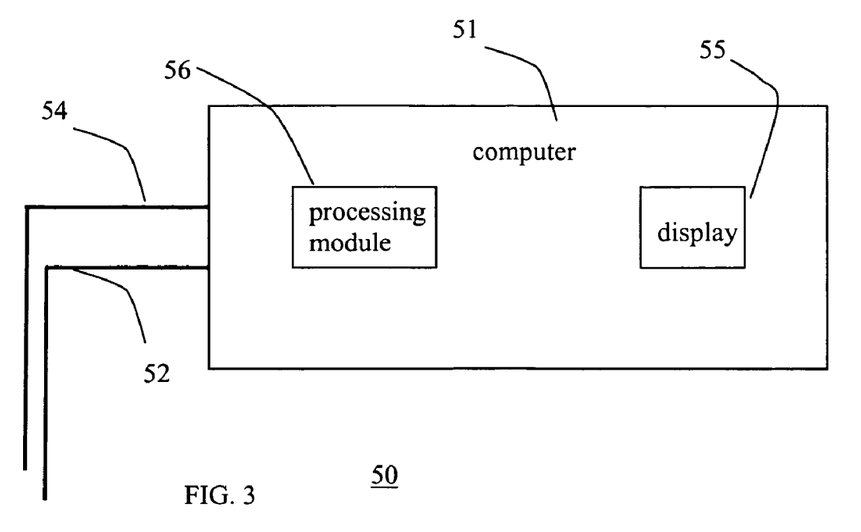
FIG. 3. shows a schematic of a system for monitoring respiration or conducting sleep studies on a patient that employs plethysmography signals obtained from the patient.

In FIG. 3, there is shown a system 50 for obtaining and processing data from a patient for purposes of diagnosing sleep apnea, or other respiratory-related sleep disorders. The system comprises a computer 51 that is configured to receive and process signals from lines 52 and 54, which are distally connected to one or more pulse oximeter probes (not shown) located on the patient. Those skilled in art will appreciate that the signals may be preprocessed to some degree by a separate signal processor and subsequently sent as one signal stream to the computer 51. Thus, the computer 51 is configured to receive signals from either lines 52 or 54 or a combination of both. Typically, one of the lines will carry power from the computer 51 to the pulse oximeter probe, while the other line carries signals back to the computer 51. The computer 51 comprises a processing module 56 with program code module(s) and/or electrical/circuitry components associated therewith to direct the processing of the signal stream from lines 52 and/or 54. The processing module 56 separates out the venous impedance component from the signal stream as described above. The processing module 56 also comprises a program code module(s) and/or electrical/circuitry components associated therewith to analyze the signal stream to determine inspiratory, expiratory, and/or air obstruction events. In a preferred embodiment, the processing module 56, or a separate processing module, is directed to generate a report indicating the frequency, duration and/or severity of air obstruction events. Each event may be given a value based on predetermined parameters. The computer can utilize the information obtained from the procedure described in Example 3 above to more accurately gauge the severity and type of air obstruction event. This information provided by the computer will enable a physician to diagnosis whether the patient has a respiratory-related sleep disorder, as well as judge the severity of such disorder, which, in turn, will enable the physician to prescribe an appropriate treatment.

Furthermore, the computer 51 comprises a display 55 showing the signal produced by the pulse oximeter probe as well as displaying information regarding the processing and/or analysis of the data from the patient. Those skilled in the art will appreciate that the display, or other suitable components, may be integral with, attached to or separate from computer 51. The computer may also comprise a control panel with a keyboard, buttons, and/or touchpad to input commands or other information. The computer may be a lightweight, portable computer apparatus that will allow the patient to conduct a sleep study at the comfort of their home. The patient is provided with the portable computer box, probe(s) and probe lines, whereby the patient can engage the probes to a central source site and conduct the testing herself.

Figure 4:
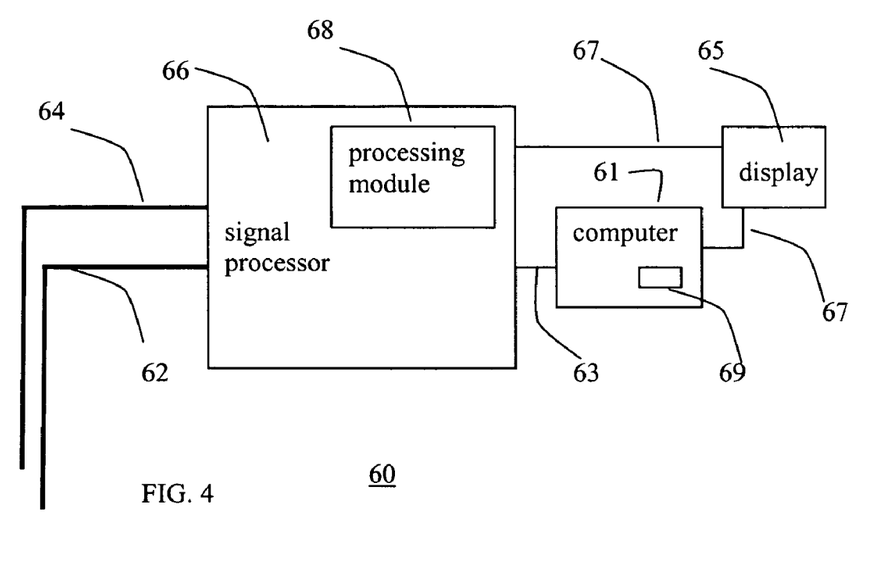
FIG. 4 shows a schematic of a system for monitoring respiration or conducting sleep studies on a patient that employs plethysmography signals obtained from the patient.

FIG. 4 is a representation of a similar system where the components are separated. Those skilled in the art will readily appreciate that two or more components of the system may be combined into a single housing unit or, alternatively, two or more components may be separate but connected through appropriate wires, or wireless communication means. The system 60 comprises a signal processor 66 which is configured to send/receive signals to/from lines 62, 64 which are connected to a pulse oximeter probe (not shown). The signal processor 66 comprises a processing module 68 configured to separate out the arterial component and venous impedance component contained in the signal stream received from the pulse oximeter probe. The arterial component signal stream and/or the venous impedance signal stream is sent to a computer 61 through line 63. The computer 61 comprises a processing module 69 to analyze the arterial component signal stream and/or venous impedance signal stream to monitor inspiratory and/or expiratory respiration events, or determine the occurrence of an abnormal respiration event. Information generated from the signal process 66 and/or computer 61 may be sent to a display 65 via lines 67.

EXAMPLE 4

Use of photoplethysmography may be employed as a surrogate for invasive CVP measurements and/or volume status. Measurement can be made of a patient who is, for instance, in an ICU, cath lab or OR and has CVP catheter in place. The airway maneuvers described above for Example 1 can be performed and the changes correlated with the CVP measurement and/or the changes in CVP seen with the airway maneuvers. At a later time, when the CVP catheter is removed, changes in the venous impedance component can be correlated with the values obtained when the CVP was in place. This should be a good indicator of the CVP and/or volume status as long as there is no change in pulmonary function/status. It is well known in the art that CVP may be used as an index for a patient's volume status.

Accordingly, in another embodiment, the subject invention pertains to a method of determining CVP without the need for a CVP catheter comprising positioning a CVP catheter in a first patient effective to produce CVP information; positioning on a central source site of said first patient a probe effective to generate a plethysmography signal stream; correlating plethysmography signal information from said probe contemporaneous to said CVP information to produce correlative CVP plethysmography information; and determining CVP in said first patient or a second patient, without having a CVP catheter in place, wherein said determining employs said correlative CVP plethysmography information. By extension, volume status of a patient may be determined through use of photoplethysmography probe without the need for a CVP catheter. Through empirical studies a relationship between the venous impedance component and CVP is determined. As this relationship is established, the need for inserting a CVP catheter for purposes of obtaining correlative CVP plethysmography information is diminished.

Accordingly, in a further embodiment, the subject invention pertains to a method of determining CVP and/or volume status of a patient comprising positioning on a central source site of a patient a probe effective to generate plethysmography information; processing said plethysmography information to produce a venous impedance component; and determining CVP and/or volume status through employing said venous impedance component.

EXAMPLE 5

Figure 5:
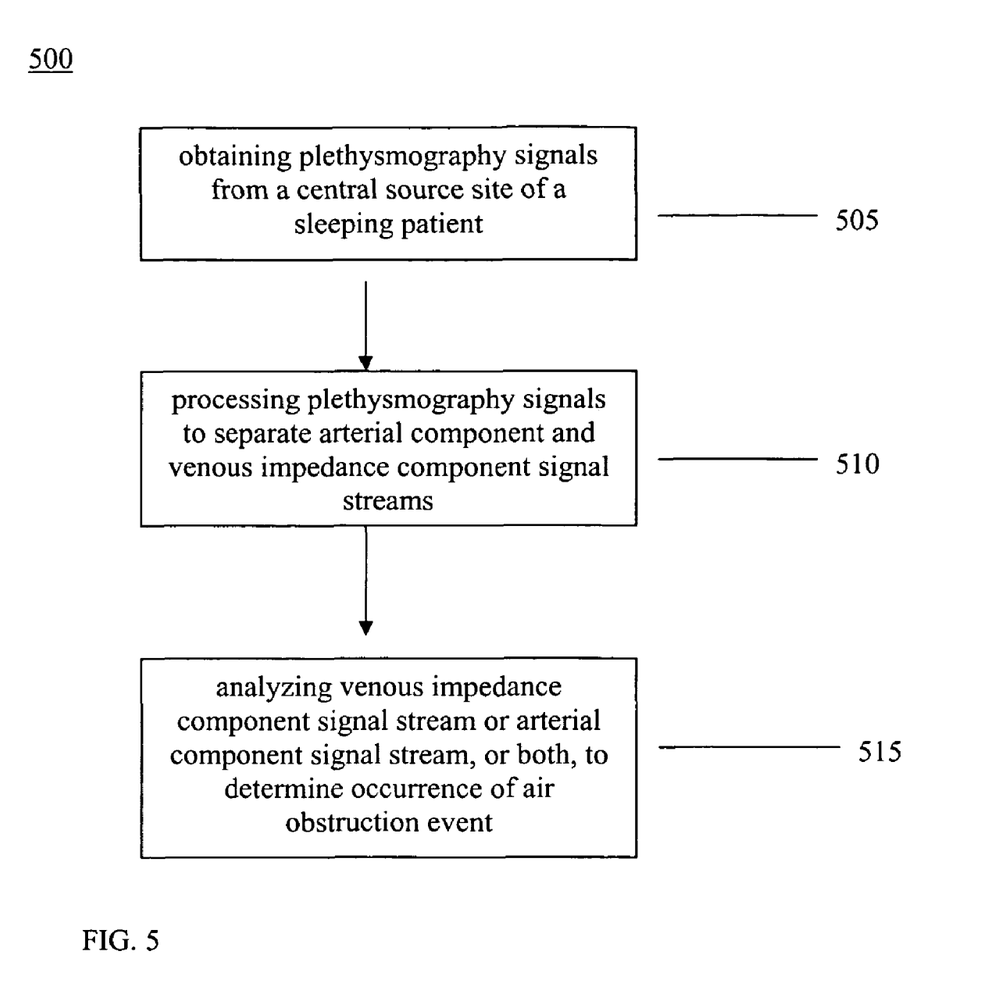
FIG. 5 shows a diagram representing a method for conducting a study to determine occurrence of abnormal respiratory events.

FIG. 5 shows diagram of one method embodiment 500 for determining the occurrence of an air obstruction event during sleep. The method 500 comprises the step of obtaining plethysmography signals from a central source site of a sleeping patient 505 and processing the plethysmography signals obtained in step 505 so that the arterial component and venous impedance component signals are separated 510. Upon the arterial component and venous impedance component signals being separated, either of the signals, or both, are analyzed to determine whether the patient has experienced any airway obstruction events 515.

EXAMPLE 6

Figure 6:
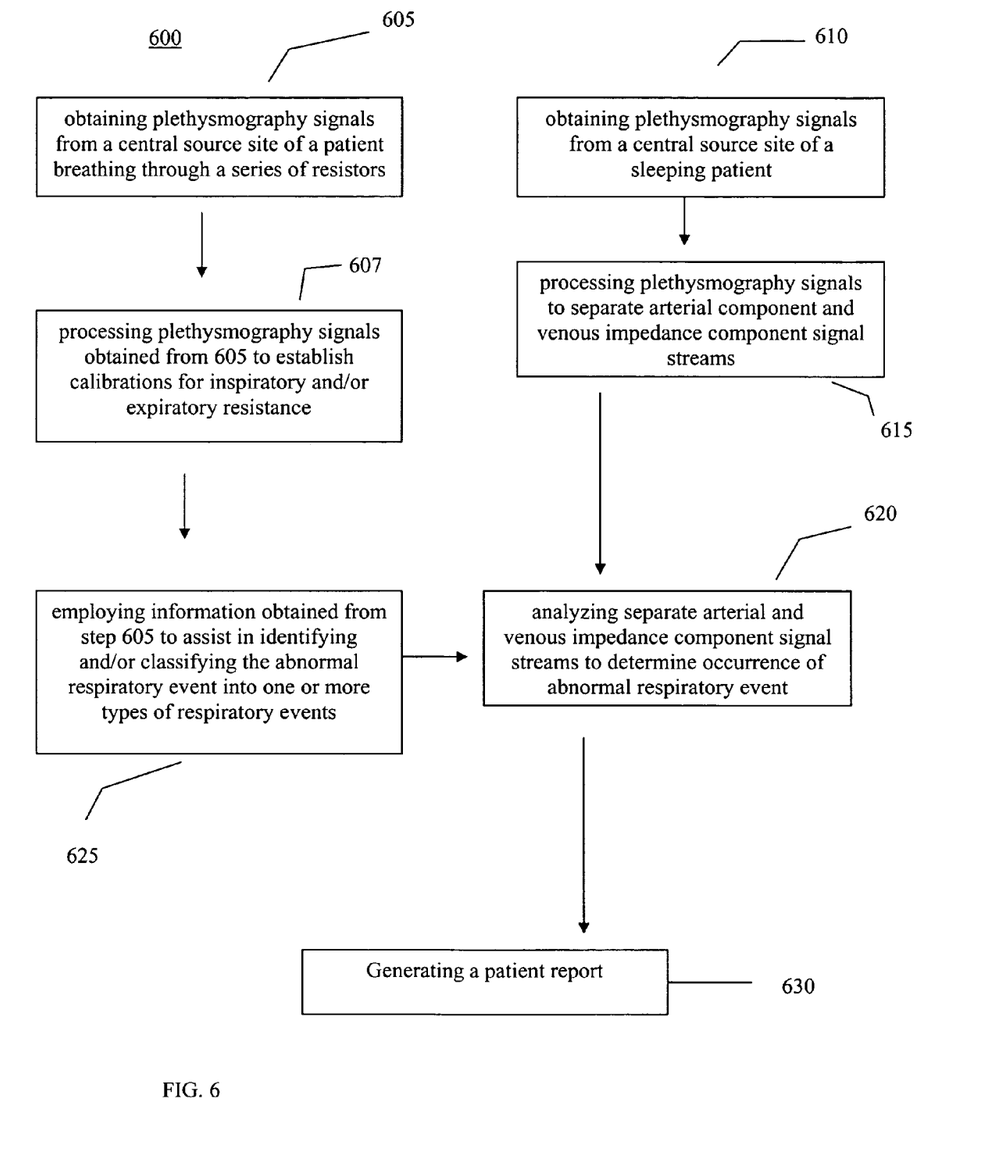
FIG. 6 shows a diagram representing a method for conducting a study to determine occurrence and magnitude of abnormal respiratory events.

FIG. 6 shows a diagram of a method embodiment 600 for determining the occurrence of an air obstruction event, including the magnitude of such event. The method comprises obtaining plethysmography signals from a central source site of a patient breathing through a series of resistors 605. The signals obtained in 605 are processed to obtain calibrations for inspiration and expiration events 607. This may involve separating out the arterial component and venous impedance component and storing information such as magnitude of the respective signals and correlating those with the resistor being used. The resistors may include a series of tubes that sequentially comprise an ever constricted airway to an ultimately blocked airway. To conduct a sleep study on a patient, plethysmography signals are obtained from a central source site of a sleeping patient 610. The plethysmography signals are processed to separate the arterial component and the venous impedance component 615. The component signal streams are then analyzed for the occurrence of any abnormal respiratory event 620. This step involves the employment of information obtained from steps 605 and 607 in order to determine the presence of such event, or the severity of such event 625. The method then optionally involves generating a report that presents the patient's respiration and the occurrence of abnormal respiration events 630.

EXAMPLE 7

Figure 7:
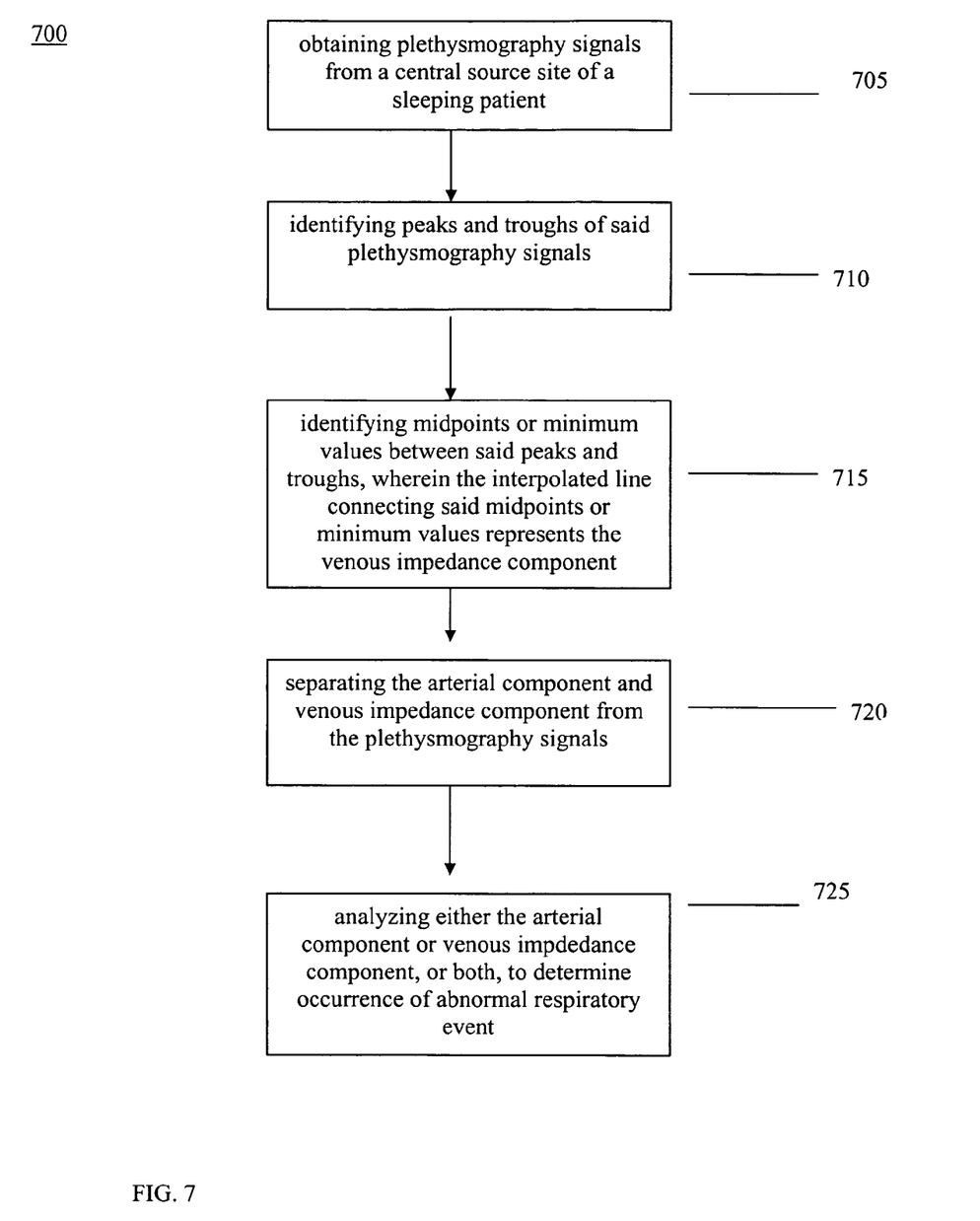
FIG. 7 shows a diagram representing a method for conducting a study to determine abnormal respiratory events.

In a more specific embodiment as diagramed in FIG. 7, the invention pertains to a method 700 of obtaining, processing and analyzing plethysmography data for purposes of identifying abnormal respiratory events during sleep. The method comprises collecting plethysmography signals from a central source site of a sleeping patient 705. Peaks and troughs of the plethysmography signals are identified 710. Next, midpoints or minimum values between the peaks and troughs identified in step 710 are identified. The interpolated line connecting these midpoints represents the venous impedance component. The arterial component and venous impedance component are separated 720, and then individually analyzed, or both analyzed to determine occurrence of abnormal respiratory event 725.

EXAMPLE 8

Figure 8:
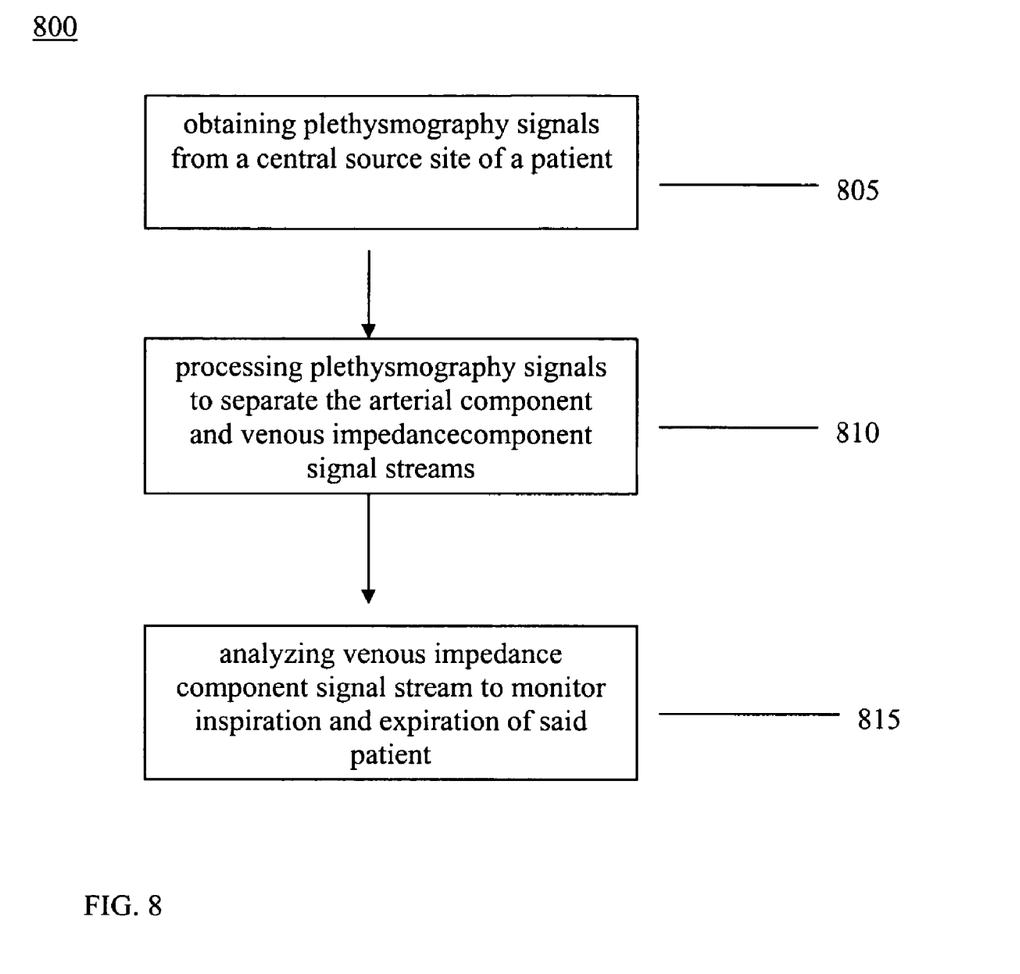
FIG. 8 shows a diagram representing a method for monitoring respiration of a patient.

FIG. 8 represents a diagram of a method embodiment 800 for monitoring respiration of a patient. In this method 800, plethsmography signals are obtained from a central source site of a patient 805. The plethsymography signals obtained from step 805 are processed to separate out the arterial component and the venous impedance component 810. The venous impedance signal stream is then analyzed to monitor inspiration and expiration of the patient 815. Naturally, the steps 805-815 are conducted in real time in order to properly monitor respiration, which is typically carried out by a computer comprising a processing module directed by program code modules.

The disclosures of the cited patent documents, publications and references are incorporated herein in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims

What is claimed is:

1. A method of monitoring respiration in a patient, said method comprising:
   securing a pulse oximeter probe to a central source site of said patient wherein said probe is configured to generate a plethysmography signal stream from said central source site;
   processing, using a computer, said signal stream received from said probe to obtain a separate arterial component signal and venous impedance component signal, wherein processing said signal stream comprises identifying peaks and troughs of said signal stream;
   identifying, using a computer, midpoints or minimum values between said peaks and troughs, wherein the interpolated line connecting said midpoints or minimum values represents said venous impedance component;
   extracting, using a computer, said venous impedance component from said signal stream thereby obtaining said separate arterial component signal and separate venous impedance component signal; and
   evaluating said arterial component signal, or venous impedance component signal, or both, to determine respiratory rate, occurrence of an inspiratory event, expiratory event, air restriction or air obstruction, or a combination thereof,
   wherein said central source site is a nasal septum, a nasal alar, a pre auricular region, a post auricular region, cheek, or ear canal of said patient.

2. The method of claim 1, wherein said central source site is the nasal septum or nasal alar.

3. The method of claim 1, wherein said evaluating comprises analyzing two or more datasets of signal information obtained at separate time periods.

4. The method of claim 1, wherein processing said signal stream information comprises processing plethysmography signal information generated while said patient is asleep.

5. A method of monitoring respiration in a patient, said method comprising:
   securing a pulse oximeter probe to a central source site of said patient wherein said probe is configured to generate a plethysmography signal stream;
   processing, using a computer, said signal stream received from said probe to obtain a venous impedance component signal, wherein processing said signal stream comprises identifying peaks and troughs of said signal stream;
   identifying, using a computer, midpoints or minimum values between said peaks and troughs, wherein the interpolated line connecting said midpoints or minimum values represents said venous impedance component;
   extracting, using a computer, said venous impedance component from said signal stream thereby obtaining said separate arterial component signal and separate venous impedance component signal; and
   observing changes in venous impedance component signal correlating with respiratory rate, inspiratory or expiratory events, or combination thereof, of said patient,
   wherein said central source site is a nasal septum, a nasal alar, a pre auricular region, a post auricular region, cheek, or ear canal of said patient.

6. A system for monitoring respiration of a patient comprising
   at least one pulse oximeter probe configured for securing to a central source site of said patient and effective to generate a plethysmography signal stream; and
   a computer communicatingly connected to said at least one pulse oximeter probe, said computer comprising at least one processing module, a first computer-readable program code module for causing said computer to process signals of said at least one pulse oximeter probe to obtain an arterial component signal or a venous impedance component signal, or both, wherein processing said signal stream comprises identifying peaks and troughs of said signal stream; identifying midpoints or minimum values between said peaks and troughs, wherein the interpolated line connecting said midpoints or minimum values represents said venous impedance component; extracting said venous impedance component from said signal stream thereby obtaining said separate arterial component signal and separate venous impedance component signal, and a second computer-readable program code module for causing said computer to analyze said arterial component signal or venous impedance component signal, or both to determine an inspiratory event, expiratory event, an air restriction event or an air obstruction event, or a combination thereof.

7. The system of claim 6, wherein said computer further comprises a display screen.

8. A computer program product for use with a computer comprising at least one processing module, said product comprising:
   a computer-usable medium comprising computer readable program code modules embodied in said computer-usable medium;
   computer readable first program code module for causing said computer to process plethysmography signals obtained from a pulse oximeter probe by separating out an arterial component signal stream and a venous impedance component signal stream, wherein processing said signal stream comprises identifying peaks and troughs of said signal stream; identifying midpoints or minimum values between said peaks and troughs, wherein the interpolated line connecting said midpoints or minimum values represents said venous impedance component; extracting said venous impedance component from said signal stream thereby obtaining said separate arterial component signal and separate venous impedance component signal; and
   computer-readable second program code module for causing said computer to analyze said arterial component signal stream or said venous impedance signal stream, or both, to determine an occurrence of an abnormal respiration event.

9. A device useful for diagnosing a respiratory condition, said device comprising a computer configured to communicate with at least one pulse oximeter probe, said computer comprising at least one processing module; a first computer-readable program code module for causing said computer to process signals of said at least one pulse oximeter probe to obtain an arterial component signal or a venous impedance component signal, or both, wherein processing said signal stream comprises identifying peaks and troughs of said signal stream; identifying midpoints or minimum values between said peaks and troughs, wherein the interpolated line connecting said midpoints or minimum values represents said venous impedance component; extracting said venous impedance component from said signal stream thereby obtaining said separate arterial component signal and separate venous impedance component signal, and a second computer-readable program code module for causing said computer to analyze said arterial component signal or venous impedance component signal, or both a respiratory condition.

10. The device of claim 9, further comprising a display screen effective to display information to a user of said device.

11. The device of claim 9, wherein said device comprises a calibrating mode and an operational mode.

12. The device of claim 11, wherein said calibrating mode allows said device to receive a first dataset of plethysmography signal information of a patient generated during respiration at a predetermined resistance, whereby said device is calibrated for said patient.

13. The device of claim 12, wherein after calibration, said device may receive a second dataset of plethysmography signal information from said patient in said operational mode such that said device may compare said second dataset with said first dataset and provide information on said display screen to assist a user of said device to diagnose a respiratory condition of said patient.

14. The device of claim 9, wherein said respiratory condition is a restriction or obstruction of the nasopharynx caused by an allergy, bacterial infection or viral infection; sleep apnea which results in a temporary partial or complete obstruction of the posterior pharynx during phases of the sleep cycle; restriction or obstruction of the trachea or bronchi caused by tracheomalacia, tracheal polyps and warts, or bronchitis; or restriction or obstruction of the lower airways, caused by asthma, viral infection, bacterial infection, cystic fibrosis or chronic obstructive pulmonary disease.

15. The device of claim 9, wherein said device weighs less than 10 kilograms, 8 kilograms, 6 kilograms, or 4 kilograms.

16. The device of claim 9, wherein said device is battery powered.

17. A method of diagnosing a respiration-related sleep disorder in a patient, said method comprising:

securing a pulse oximeter probe to a central source site of said patient wherein said probe is configured to generate a plethysmography signal stream from said central source site;

processing, using a computer, said signal stream received from said probe to obtain a separate arterial component signal and venous impedance component signal, wherein processing said signal stream comprises identifying peaks and troughs of said signal stream;

identifying, using a computer, midpoints or minimum values between-said peaks and troughs, wherein the interpolated line connecting said midpoints or minimum values represents said venous impedance component;

extracting, using a computer, said venous impedance component from said signal stream thereby obtaining said separate arterial component signal and separate venous impedance component signal and wherein processing said signal stream information comprises processing plethysmography signal information generated while said patient is asleep; and evaluating said arterial component signal, or venous impedance component signal, or both, to determine occurrence of an inspiratory event, expiratory event, air restriction or air obstruction, or a combination thereof, wherein said central source site is a nasal septum, a nasal alar, a pre-auricular region, a post auricular region, cheek, or ear canal of said patient.

* * * * *